United States Patent
Moody, III et al.

(10) Patent No.: US 12,415,012 B2
(45) Date of Patent: Sep. 16, 2025

(54) NONWOVEN FABRICS HAVING IMPROVED SOFTNESS

(71) Applicant: Berry Global, Inc., Evansville, IN (US)

(72) Inventors: Ralph A. Moody, III, Mooresville, NC (US); Abhay Joijode, Huntersville, NC (US); Mehmet Selcuk Sinangil, Mooresville, NC (US)

(73) Assignee: MAGNERA CORPORATION, Charlotte, NC (US)

( * ) Notice: Subject to any disclaimer, the term of this patent is extended or adjusted under 35 U.S.C. 154(b) by 423 days.

(21) Appl. No.: 17/858,258

(22) Filed: Jul. 6, 2022

(65) Prior Publication Data
US 2023/0015896 A1 Jan. 19, 2023

Related U.S. Application Data (60) Provisional application No. 63/257,209, filed on Oct. 19, 2021, provisional application No. 63/219,147, filed on Jul. 7, 2021.

(51) Int. Cl.
*A61L 15/20* (2006.01)
*A61L 15/24* (2006.01)
(Continued)

(52) U.S. Cl.
CPC .............. *A61L 15/24* (2013.01); *B32B 5/022* (2013.01); *B32B 5/267* (2021.05); *B32B 5/269* (2021.05);
(Continued)

(58) Field of Classification Search
CPC ....................................................... A61L 15/24
See application file for complete search history.

(56) References Cited

U.S. PATENT DOCUMENTS

| 5,266,392 | A |  | 11/1993 | Land et al. |
| 5,714,107 | A | * | 2/1998 | Levy ..................... D04H 1/54 |
| | | | | 264/289.3 |

(Continued)

FOREIGN PATENT DOCUMENTS

| WO | 1999055942 A1 | 11/1999 |
| WO | 2018017169 A1 | 1/2018 |

OTHER PUBLICATIONS

Second Written Opinion issued in corresponding international application No. PCT/US2022/036185 on May 16, 2023, all enclosed pages cited herein.

(Continued)

*Primary Examiner* — Catharine L Anderson
(74) *Attorney, Agent, or Firm* — BURR & FORMAN (57) ABSTRACT

Nonwoven fabrics are provided that include a plurality of mono-component spunbond fibers comprising a polymeric material including a polymeric blend of (i) a TS7 value of at most about 30 as determined by a Tissue Softness Analyzer (TSA) from Emtec Innovative Testing Solutions; (ii) a HF value of at least about 40 as determined by a Tissue Softness Analyzer (TSA) from Emtec Innovative Testing Solutions; (iii) a delta value of at least 20, wherein the delta value is determined by subtracting the TS7 value from the HF value; (iv) a TS7 value that is from about 5% to about 35% lower than that of an identically constructed nonwoven fabric formed from 100% polypropylene; and (v) a HF value that is from about 5% to about 35% larger than that of an identically constructed nonwoven fabric formed from 100% polypropylene.

14 Claims, 3 Drawing Sheets

(51) Int. Cl.
    *B32B 5/02*     (2006.01)
    *B32B 5/26*     (2006.01)
    *D04H 1/4291*     (2012.01)
    *D04H 1/56*     (2006.01)

(52) U.S. Cl.
    CPC ............ *D04H 1/4291* (2013.01); *D04H 1/56* (2013.01); *B32B 2250/20* (2013.01); *B32B 2262/0253* (2013.01); *B32B 2555/02* (2013.01); *D10B 2321/021* (2013.01); *D10B 2321/022* (2013.01); *D10B 2509/026* (2013.01)

(56) References Cited

U.S. PATENT DOCUMENTS

| | | | |
|---|---|---|---|
| 11,179,280 B2 * | 11/2021 | Lakso | ................ A61F 13/4753 |
| 2012/0329351 A1 | 12/2012 | Mehta et al. | |
| 2014/0276517 A1 | 9/2014 | Chester | |
| 2017/0009401 A1 | 1/2017 | Stickney et al. | |
| 2018/0216269 A1 | 8/2018 | Ashraf et al. | |
| 2022/0192897 A1 * | 6/2022 | Whitely | ................ A61F 13/496 |

OTHER PUBLICATIONS

Third Written Opinion issued in corresponding international application No. PCT/US2022/036185 on Jul. 25, 2023, all enclosed pages cited herein.

International Search Report and Written Opinion issued in corresponding international application No. PCT/US2022/036185 on Nov. 8, 2022, all enclosed pages cited herein.

Intention to Grant issued in corresponding European Patent Application No. 22748611.5 mailed Dec. 13, 2024, all pages cited in its entirety.

Extended European Search Report issued in European Application No. 25169595.3 on May 22, 2025, all enclosed pages cited.

* cited by examiner

NONWOVEN FABRICS HAVING IMPROVED SOFTNESS

CROSS-REFERENCE TO RELATED APPLICATIONS

This application claims priority under 35 U.S.C. § 119 to U.S. Patent Application No. 63/219,147 filed Jul. 7, 2021 and 63/257,209 filed on Oct. 19, 2021, each of which being expressly incorporated by reference herein in their entirety.

TECHNICAL FIELD

Embodiments of the presently-disclosed invention relate generally to nonwoven fabrics having a plurality of mono-component spunbond fibers comprising a polymeric material including a polymeric blend of (i) at least one polypropylene polymer, (ii) at least one polyethylene polymer, and (iii) at least one compatibilizer comprising at least one polypropylene-polyethylene copolymer, in which the nonwoven fabrics have improved softness and hand feel.

BACKGROUND

A variety of personal hygiene products require a topsheet or the like that is soft to the touch to provide comfort to the user and/or reduces skin irritation associated with extended use of such personal hygiene products.

SUMMARY OF INVENTION

One or more embodiments of the invention may address one or more of the aforementioned problems. Certain embodiments according to the invention provide a nonwoven fabric including a plurality of mono-component spunbond fibers comprising a polymeric material including a polymeric blend of (i) at least one polypropylene polymer, (ii) at least one polyethylene polymer, and (iii) at least one compatibilizer comprising or consisting of at least one polypropylene-polyethylene copolymer. The nonwoven fabric may have one or more of the following: (i) a TS7 value of at most about 30 as determined by a Tissue Softness Analyzer (TSA) from Emtec Innovative Testing Solutions; (ii) a HF value of at least about 40 as determined by a Tissue Softness Analyzer (TSA) from Emtec Innovative Testing Solutions; (iii) a delta value of at least 20, wherein the delta value is determined by subtracting the TS7 value from the HF value; (iv) a TS7 value that is from about 5% to about 35% lower than that of an identically constructed nonwoven fabric formed from 100% polypropylene (e.g., the same polypropylene used in the polymeric blend); and (v) a HF value that is from about 5% to about 35% larger than that of an identically constructed nonwoven fabric formed from 100% polypropylene (e.g., the same polypropylene used in the polymeric blend).

In another aspect, the present invention provides a method of making a nonwoven fabric. The method may comprise the following: (a) forming a polymeric melt including a polymeric blend of (i) at least one polypropylene polymer, (ii) at least one polyethylene polymer, and (iii) at least one polypropylene-polyethylene copolymer; (b) forming a plurality of mono-component spunbond fibers via melt-spinning the polymeric melt; and (c) consolidating the plurality of mono-component spunbond fibers to form a nonwoven fabric in accordance with nonwoven fabrics as described and disclosed herein.

In yet another aspect, the present invention provides an article comprising one or more nonwoven fabrics as described and disclosed herein. The article may comprise an adult diaper, a baby diaper, a pull-up, of a feminine hygiene pad. In accordance with certain embodiments of the invention, the article may comprise a topsheet comprising a nonwoven fabric as described and disclosed herein.

BRIEF DESCRIPTION OF THE DRAWING(S)

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout, and wherein.

DETAILED DESCRIPTION

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present invention provides a nonwoven fabric including a plurality of mono-component spunbond fibers comprising a polymeric material including a polymeric blend of (i) at least one polypropylene polymer, (ii) at least one polyethylene polymer, and (iii) at least one compatibilizer comprising or consisting of at least one polypropylene-polyethylene copolymer. In this regard, the presence of the polyethylene in the polymeric blend impacts the melting point of a nonwoven web (e.g., unconsolidated mono-component fibers) and/or the nonwoven fabric (e.g., already consolidated to at least some degree). That is, the presence of the polyethylene in the polymeric blend lowers the onset of melting and/or softening of the mono-component fibers forming the nonwoven web (e.g., unconsolidated mono-component fibers) and/or the nonwoven fabric (e.g., already consolidated nonwoven fabric that may be bonded to a separate nonwoven layer or a separate film layer). Accordingly, a nonwoven web formed from the mono-component spunbond fibers may be thermally bonded (e.g., ultrasonic bonded, thermal calendering, etc.) at reduced temperatures, which provides energy savings as well as good tensile properties at lower bond temperatures. In addition, the reduced onset of melting temperature (e.g., softening and/or melting initiates at a lower temperature) provides valuable benefits when attempting lamination with lower melt structures, such as polyethylene films, allowing lower processing energy, and less chance of film damage/holes at bonding sites.

Additionally, the reduced onset of melting temperature is further advantageous when utilized in a spunbond-meltblown-spunbond (SMS) nonwoven fabric. This is due to the suppression of the melt point of the spunbond layer or layers, such as those described and disclosed herein. When running SMS constructs, if the melting point of the spunbond fibers are similar to that of the meltblown fibers it is often easy to bond at conditions for optimum tensile that would damage the smaller diameter meltblown fibers as they have less mass, causing "pinholes" and lower hydrostatic head values on barrier performance. In accordance with certain embodiments of the invention, by lowering the onset of the melting point of the spunbond fibers, desirable tensile strengths in a bonding curve may be achieved, but stay below the point of physical "pin-holing" of the meltblown structure. In this regard, the certain embodiments of the invention may improve both tensile strength while retaining hydrostatic head values. Moreover, the reduction in the onset of melting for the spunbond mono-component fibers may also be valuable in porosity measurements, such as maximum pore size reduction due to the prevention of small pinholes that can be created in the meltblown structure.

In accordance with certain embodiments of the invention, the nonwoven fabric may be provided as a component of a composite structure, such as a SMS-type nonwoven fabric or a nonwoven-film laminate.

The terms "substantial" or "substantially" may encompass the whole amount as specified, according to certain embodiments of the invention, or largely but not the whole amount specified (e.g., 95%, 96%, 97%, 98%, or 99% of the whole amount specified) according to other embodiments of the invention.

The terms "polymer" or "polymeric", as used interchangeably herein, may comprise homopolymers, copolymers, such as, for example, block, graft, random, and alternating copolymers, terpolymers, etc., and blends and modifications thereof. Furthermore, unless otherwise specifically limited, the term "polymer" or "polymeric" shall include all possible structural isomers; stereoisomers including, without limitation, geometric isomers, optical isomers or enantiomers; and/or any chiral molecular configuration of such polymer or polymeric material. These configurations include, but are not limited to, isotactic, syndiotactic, and atactic configurations of such polymer or polymeric material. The term "polymer" or "polymeric" shall also include polymers made from various catalyst systems including, without limitation, the Ziegler-Natta catalyst system and the metallocene/single-site catalyst system. The term "polymer" or "polymeric" shall also include, in according to certain embodiments of the invention, polymers produced by fermentation process or biosourced.

The terms "nonwoven" and "nonwoven web", as used herein, may comprise a web having a structure of individual fibers, filaments, and/or threads that are interlaid but not in an identifiable repeating manner as in a knitted or woven fabric. Nonwoven fabrics or webs, according to certain embodiments of the invention, may be formed by any process conventionally known in the art such as, for example, meltblowing processes, spunbonding processes, needle-punching, hydroentangling, air-laid, and bonded carded web processes. A "nonwoven web", as used herein, may comprise a plurality of individual fibers that have not been subjected to a consolidating process.

The terms "fabric" and "nonwoven fabric", as used herein, may comprise a web of fibers in which a plurality of the fibers are mechanically entangled or interconnected, fused together, and/or chemically bonded together. For example, a nonwoven web of individually laid fibers may be subjected to a bonding or consolidation process to bond at least a portion of the individually fibers together to form a coherent (e.g., united) web of interconnected fibers.

The term "consolidated" and "consolidation", as used herein, may comprise the bringing together of at least a portion of the fibers of a nonwoven web into closer proximity or attachment there-between (e.g., thermally fused together, chemically bonded together, and/or mechanically entangled together) to form a bonding site, or bonding sites, which function to increase the resistance to external forces (e.g., abrasion and tensile forces), as compared to the unconsolidated web. The bonding site or bonding sites, for example, may comprise a discrete or localized region of the web material that has been softened or melted and optionally subsequently or simultaneously compressed to form a discrete or localized deformation in the web material. Furthermore, the term "consolidated" may comprise an entire nonwoven web that has been processed such that at least a portion of the fibers are brought into closer proximity or attachment there-between (e.g., thermally fused together, chemically bonded together, and/or mechanically entangled together), such as by thermal bonding or mechanical entanglement (e.g., hydroentanglement) as merely a few examples. Such a web may be considered a "consolidated nonwoven", "nonwoven fabric" or simply as a "fabric" according to certain embodiments of the invention.

The term "staple fiber", as used herein, may comprise a cut fiber from a filament. In accordance with certain embodiments, any type of filament material may be used to form staple fibers. For example, staple fibers may be formed from polymeric fibers, and/or elastomeric fibers. Non-limiting examples of materials may comprise polyolefins (e.g., a polypropylene or polypropylene-containing copolymer), polyethylene terephthalate, and polyamides. The average length of staple fibers may comprise, by way of example only, from about 2 centimeter to about 15 centimeter.

The term "spunbond", as used herein, may comprise fibers which are formed by extruding molten thermoplastic material as filaments from a plurality of fine, usually circular, capillaries of a spinneret with the diameter of the extruded filaments then being rapidly reduced. According to an embodiment of the invention, spunbond fibers are generally not tacky when they are deposited onto a collecting surface and may be generally continuous as disclosed and described herein. It is noted that the spunbond used in certain composites of the invention may include a nonwoven described in the literature as SPINLACE®. Spunbond fibers, for example, may comprises continuous fibers.

As used herein, the term "continuous fibers" refers to fibers which are not cut from their original length prior to being formed into a nonwoven web or nonwoven fabric. Continuous fibers may have average lengths ranging from greater than about 15 centimeters to more than one meter, and up to the length of the web or fabric being formed. For example, a continuous fiber, as used herein, may comprise a fiber in which the length of the fiber is at least 1,000 times larger than the average diameter of the fiber, such as the length of the fiber being at least about 5,000, 10,000, 50,000, or 100,000 times larger than the average diameter of the fiber.

The term "meltblown", as used herein, may comprise fibers formed by extruding a molten thermoplastic material through a plurality of fine die capillaries as molten threads or filaments into converging high velocity, usually hot, gas (e.g. air) streams which attenuate the filaments of molten thermoplastic material to reduce their diameter, which may be to microfiber diameter, according to certain embodiments of the invention. According to an embodiment of the invention, the die capillaries may be circular. Thereafter, the meltblown fibers are carried by the high velocity gas stream and are deposited on a collecting surface to form a web of randomly disbursed meltblown fibers. Meltblown fibers may comprise microfibers which may be continuous or discontinuous and are generally tacky when deposited onto a collecting surface. Meltblown fibers, however, are shorter in length than those of spunbond fibers.

The term "layer", as used herein, may comprise a generally recognizable combination of similar material types and/or functions existing in the X-Y plane.

The term "multi-component fibers", as used herein, may comprise fibers formed from at least two different polymeric materials (e.g., two or more) extruded from separate extruders but spun together to form one fiber. The term "bi-component fibers", as used herein, may comprise fibers formed from two different polymeric materials extruded from separate extruders but spun together to form one fiber. The polymeric materials or polymers are arranged in a substantially constant position in distinct zones across the cross-section of the multi-component fibers and extend continuously along the length of the multi-component fibers. The configuration of such a multi-component fibers may be, for example, a sheath/core arrangement wherein one polymer is surrounded by another, or may be a side-by-side arrangement, a pie arrangement, or an "islands-in-the-sea" arrangement, each as is known in the art of multicomponent, including bicomponent, fibers.

The term "monocomponent fibers", as used herein may comprise fibers formed from a single polymer or polymeric blend (e.g., a blend or mixture of two or more polymers) extruded from a single extruder. The single polymer or polymeric blend, for example, may define a polymeric matrix in which one or more additives (e.g., fillers) may be dispersed.

The term "machine direction" or "MD", as used herein, comprises the direction in which the fabric produced or conveyed. The term "cross-direction" or "CD", as used herein, comprises the direction of the fabric substantially perpendicular to the MD.

As used herein, the term "aspect ratio", comprise a ratio of the length of the major axis to the length of the minor axis of the cross-section of the fiber in question.

All whole number end points disclosed herein that can create a smaller range within a given range disclosed herein are within the scope of certain embodiments of the invention. By way of example, a disclosure of from about 10 to about 15 includes the disclosure of intermediate ranges, for example, of: from about 10 to about 11; from about 10 to about 12; from about 13 to about 15; from about 14 to about 15; etc. Moreover, all single decimal (e.g., numbers reported to the nearest tenth) end points that can create a smaller range within a given range disclosed herein are within the scope of certain embodiments of the invention. By way of example, a disclosure of from about 1.5 to about 2.0 includes the disclosure of intermediate ranges, for example, of: from about 1.5 to about 1.6; from about 1.5 to about 1.7; from about 1.7 to about 1.8; etc.

In one aspect, the present invention provides a nonwoven fabric including a plurality of mono-component spunbond fibers comprising a polymeric material including a polymeric blend of (i) at least one polypropylene polymer, (ii) at least one polyethylene polymer, and (iii) at least one compatibilizer comprising or consisting of at least one polypropylene-polyethylene copolymer. The nonwoven fabric may have one or more of the following: (i) a TS7 value of at most about 30 as determined by a Tissue Softness Analyzer (TSA) from Emtec Innovative Testing Solutions; (ii) a HF value of at least about 40 as determined by a Tissue Softness Analyzer (TSA) from Emtec Innovative Testing Solutions; (iii) a delta value of at least 20, wherein the delta value is determined by subtracting the TS7 value from the HF value; (iv) a TS7 value that is from about 5% to about 35% lower than that of an identically constructed nonwoven fabric (e.g., identical basis weight, identical bonding pattern, identical bonded area, etc.) formed from 100% polypropylene (e.g., the same polypropylene used in the polymeric blend); and (v) a HF value that is from about 5% to about 35% larger than that of an identically constructed nonwoven fabric (e.g., identical basis weight, identical bonding pattern, identical bonded area, etc.) formed from 100% polypropylene (e.g., the same polypropylene used in the polymeric blend). The softness values determined by the TSA includes "T57" data, which is a direct measurement of the softness of the sample (e.g., via measurement of blade vibration by the TSA device due to the stiffness of the fibers). The "HF" values are composite values based on the "T57" data, a "TS750" data, and "D" data. The "HF" values provide an objective evaluation of the samples overall hand-feel. "TS750" data is a direct measurement of the samples roughness (e.g., via measurement of vertical vibrations from the sample by the TSA device due to horizontal blade movement across the surface of the sample. The "D" data is a direct measurement of the stiffness of the sample by the TSA device due to the sample deformation under a defined force.

In accordance with certain embodiments of the invention, the nonwoven fabric has a TS7 value from about 2 to about 50, such as at least about any of the following: 2, 3, 4, 5, 6, 8, 10, 12, 14, 15, 16, 18, 19, 20, 21, 22, 23, 24, and 25, and/or at most about any of the following: 50, 45, 40, 35, 30, 29, 28, 27, 26, and 25. Additionally or alternatively, the nonwoven fabric has a HF value from about 40 to about 120, such as at least about any of the following: 40, 42, 44, 46, 48, 50, 52, 54, 56, 58, 60, 65, and 70, and/or at most about any of the following: 120, 115, 110, 105, 100, 95, 90, 85, 80, 75, and 70. Additionally or alternatively, the nonwoven fabric has a delta value is from about 20 to about 75, such as at least about any of the following: 20, 22, 24, 26, 28, 30, 32, 34, and 35, and/or at most about any of the following: 75, 70, 65, 60, 55, 50, 45, 44, 42, 40, 38, 36, and 35.

In accordance with certain embodiments of the invention, the nonwoven fabric has a TS7 value that is from about 5% to about 35% lower than that of an identically constructed nonwoven fabric (e.g., identical basis weight, identical bonding pattern, identical bonded area, etc.) formed from 100% polypropylene (e.g., the same polypropylene used in the polymeric blend), such as at least about any of the following: 5, 6, 8, 10, 12, 14, and 15% lower, and/or at most about 35, 30, 25, 24, 22, 20, 18, 16, and 15% lower. In this regard, the TS7 value for the nonwoven fabric has in increased softness relative to an identically constructed nonwoven fabric (e.g., identical basis weight, identical bonding pattern, identical bonded area, etc.) formed from 100% polypropylene (e.g., the same polypropylene used in the polymeric blend) as evidenced by the reduced/lower TS7 value. By way of example only, the nonwoven fabric in accordance with certain embodiments of the invention may have a TS7 value of 24, while an identically constructed nonwoven fabric formed from 100% polypropylene (e.g., the same polypropylene used in the polymeric blend) may have a TS7 value of 31 (e.g., about 29% lower TS7 value for the nonwoven fabric in accordance with certain embodiments of the invention).

In accordance with certain embodiments of the invention, the nonwoven fabric has a HF value that is from about 5% to about 35% larger than that of an identically constructed nonwoven fabric formed from 100% polypropylene (e.g., the same polypropylene used in the polymeric blend), such as at least about any of the following: 5, 6, 8, 10, 12, 14, and 15% larger, and/or at most about 35, 30, 25, 24, 22, 20, 18, 16, and 15% larger. In this regard, the HF value for the nonwoven fabric has in increased overall hand feel relative to an identically constructed nonwoven fabric formed from 100% polypropylene (e.g., the same polypropylene used in the polymeric blend) as evidenced by the increased/larger HF value. By way of example only, the nonwoven fabric in accordance with certain embodiments of the invention may have a HF value of 60, while an identically constructed nonwoven fabric formed from 100% polypropylene (e.g., the same polypropylene used in the polymeric blend) may have a HF value of 46 (e.g., about 27% larger HF value for the nonwoven fabric in accordance with certain embodiments of the invention).

In accordance with certain embodiments of the invention, the polymeric blend may comprise from about 60 to about 90 wt. % of the at least one polypropylene polymer, such as at least about any of the following: 60, 62, 64, 65, 66, 68, 70, 72, 74, 77, 78, and 80 wt. % of the at least one polypropylene polymer, and/or at most about any of the following: 90, 88, 86, 85, 84, 83, 82, 81, and 80 wt. % of the at least one polypropylene polymer. The at least one polypropylene polymer, for example, may be a first polypropylene polymer (e.g., a single polypropylene polymer).

The at least one polypropylene polymer, in accordance with certain embodiments of the invention, may have a melt flow rate (MFR) of from about 10 to about 100 g/10 min as determined by ASTM D1238 (230° C./2.16 kg), such as at least about any of the following: 10, 12, 14, 16, 18, 20, 22, 24, 25, 26, 28, 30, 32, 34, 35, 36, 38, 40, 42, 44, 45, 46, 48, and 50 g/10 min, and/or at most about any of the following: 100, 95, 90, 85, 80, 75, 70, 65, 60, 58, 56, 55, 54, 52, and 50 g/10 min.

In accordance with certain embodiments of the invention, the polymeric blend may comprise from about 5 to about 30 wt. % of the at least one polyethylene polymer, such as at least about any of the following: 5, 6, 8, 10, 12, 14, and 15 wt. % of the at least one polyethylene polymer, and/or at most about any of the following: 30, 28, 26, 25, 24, 22, 20, 18, 16, and 15 wt. % of the at least one polyethylene polymer. The at least one polyethylene polymer, for example, may be a first polyethylene polymer (e.g., a single polyethylene polymer).

The at least one polyethylene polymer, in accordance with certain embodiments of the invention, may have a melt flow rate (MFR) of from about 1 to about 30 g/10 min as determined by ASTM D1238 (190° C./2.16 kg), such as at least about any of the following: 1, 2, 4, 5, 6, 8, 10, 12, 14, and 15 g/10 min, and/or at most about any of the following: 30, 25, 20, 18, 16, and 15 g/10 min.

In accordance with certain embodiments of the invention, the polymeric blend may comprise from about 1 to about 10 wt. % of the at least one polypropylene-polyethylene copolymer, such as at least about any of the following: 1, 2, 3, 4, and 5 wt. % of the at least one polypropylene-polyethylene copolymer, and/or at most about any of the following: 10, 9, 8, 7, 6, and 5 wt. % of the at least one polypropylene-polyethylene copolymer. The at least one polypropylene-polyethylene copolymer, for example, may be a first polypropylene-polyethylene copolymer (e.g., a single polypropylene-polyethylene copolymer).

The first polypropylene-polyethylene copolymer may comprise a first block copolymer or a first random copolymer. In accordance with certain embodiments of the invention, the first polypropylene-polyethylene copolymer is an EP-iPP diblock polymer.

The first polypropylene-polyethylene copolymer, in accordance with certain embodiments of the invention, may have an ethylene monomer content from about 5 to about 60% by weight, such as at least about any of the following: 5, 6, 8, 10, 12, 14, 15, 16, 18, 20, 22, 24, 25, 26, 28, 30, 32, 34, 35, 26, 38, 40, 42, 44, and 45% by weight, and/or at most about any of the following: 60, 58, 56, 55, 54, 52, 50, 48, 46, and 45% by weight. Additionally or alternatively, the at least one polypropylene-polyethylene copolymer (e.g., first polypropylene-polyethylene copolymer) may have a melt flow rate (MFR) of from about 0.5 g/10 min to about 20 g/10 min as determined by ASTM D1238 (230° C./2.16 kg), such as at least about the any of the following: 0.5, 1, 1.5, 2, 2.5, 3, 3.5, 4, 4.5, 5, 5.5, 6, 6.5, 7, 7.5, 8, 8.5, 9, 9.5, and 10 g/10 min as determined by ASTM D1238 (230° C./2.16 kg), and/or at most about any of the following: 20, 19, 18, 17, 16, 15, 14, 13, 12, 11, and 10 g/10 min as determined by ASTM D1238 (230° C./2.16 kg).

In this regard, recent advances in single-site catalysts (e.g., metallocene catalysts) have allowed creation of variety of polymer structures that were difficult or impossible to create economically. In this regard, the first polypropylene-polyethylene copolymer may comprise a copolymer formed from a single-site catalyst, such as a metallocene-catalyzed copolymer. For example, polypropylene-based polymers with significant amounts of ethylene content can be produced in a variety of configurations (e.g., well-defined blocks) to further enhance the copolymers' ability to bridge the generally immiscible polymers. An example of such a material includes Vistamaxx™ (e.g., Vistamaxx™ 6202), a polypropylene-based elastomer that comprises a copolymer of propylene and ethylene. These propylene-based elastomers, for example, comprise isotactic polypropylene microcrystalline regions and random amorphous regions (e.g., ethylene). Such olefinic copolymers may comprise hard blocks and soft blocks, where the hard blocks are primarily propylene and the soft blocks are primarily ethylene. In this regard, the hard blocks (e.g., propylene) may comprise 10-90% by weight of the copolymer while the soft blocks may comprise from 90-10% by weight of the copolymer. In this regard, these copolymers include a random ethylene distribution throughout the copolymer. Vistamaxx™ (e.g., Vistamaxx™ 6202) copolymers are commercially available from ExxonMobil. Vistamaxx™ 6202 has a density of 0.862 g/cc, a MI (190 C/2.16 kg) of 9.1, a MFR (230 C/2.16 kg load) of 20, and an ethylene content of 15% by weight. An additional example includes an olefin diblock copolymer comprising an EP-iPP diblock polymer such as Intune™, which is a polypropylene-based block copolymer including ethylene monomers. In accordance with certain embodiments of the invention, the first polypropylene-polyethylene copolymer disclosed herein may be prepared, for example, by a process comprising contacting an addition polymerizable monomer or mixture of monomers under addition polymerization conditions with a composition comprising at least one addition polymerization catalyst, a co-catalyst and a chain shuttling agent ("CSA"), in which the process is characterized by formation of at least some of the growing polymer chains under differentiated process conditions in two or more reactors operating under steady state polymerization conditions or in two or more zones of a reactor operating under plug flow polymerization conditions. In accordance with certain embodiments of the invention, the first polypropylene-polyethylene copolymer may comprise an olefin block copolymer formed from a single-site catalyst or other catalyst systems. That is, the first polypropylene-polyethylene copolymer may not be produced from a single-site catalyst in accordance with certain embodiments of the invention. In accordance with certain embodiments of the invention, the first polypropylene-polyethylene copolymer is devoid of anhydride functionality, such as maleic anhydride functionality.

In accordance with certain embodiments of the invention, the copolymers formed from a single-site catalyst as discussed above may be differentiated from conventional, random copolymers, physical blends of polymers, and block copolymers prepared via sequential monomer addition. These copolymers may be differentiated from random copolymers by characteristics such as higher melting temperatures for a comparable amount of comonomer, block composite index, as described below; differentiated from a physical blend by characteristics such as block composite index, better tensile strength, improved fracture strength, finer morphology, improved optics, and greater impact strength at lower temperature; differentiated from block copolymers prepared by sequential monomer addition by molecular weight distribution, rheology, shear thinning, rheology ratio, and in that there is block polydispersity.

By way of further examples, the first polypropylene-polyethylene copolymer may comprise an EP-iPP diblock polymer that has an ethylene content from 43 to 48% by weight, or from 43.5 to 47% by weight, or from 44 to 47% by weight, based on the weight of the diblock copolymer. In an example embodiment, the EP-iPP diblock polymer may have a propylene content from 57 to 52% by weight, or from 56.5 to 53% by weight, or from 56 to 53% by weight, based on the weight of the EP-iPP diblock polymer.

In accordance with certain embodiments of the invention, the polymeric blend has a first MFR ratio between a first MFR of the at least one polypropylene polymer as determined by ASTM D1238 (230° C./2.16 kg) and a second MFR of the at least one polyethylene polymer as determined by ASTM D1238 (230° C./2.16 kg) is from about 5:1 to about 20:1, such as at least about any of the following: 5:1, 6:1, 7:1, 8:1, 9:1, 10:1, 11:1, and 12:1, and/or at most about any of the following: 20:1, 19:1, 18:1, 17:1, 16:1, 15:1, 14:1, 13:1, and 12:1.

In accordance with certain embodiments of the invention, the polymeric blend has a MFR from about 20 to about 60 g/10 min as determined by ASTM D1238 (230° C./2.16 kg), such as at least about any of the following: 20, 22, 24, 25, 26, 28, 30, 32, 34, 35, 36, 38, and 40 g/10 min as determined by ASTM D1238 (230° C./2.16 kg), and/or at most about any of the following: 60, 59, 58, 56, 55, 54, 52, 50, 49, 48, 47, 46, 45, 44, 43, 42, 41, and 40 g/10 min as determined by ASTM D1238 (230° C./2.16 kg).

In accordance with certain embodiments of the invention, the plurality of mono-component spunbond fibers have an average diameter from about 10 to about 30 microns, such as at least about any of the following: 10, 12, 14, 15, 16, 18, and 20 microns, and/or at most about any of the following: 30, 28, 26, 25, 24, 22, and 20 microns.

The polymeric material, in accordance with certain embodiments of the invention, may further comprises a compatibilizer comprising an anhydride functionality, such as maleic anhydride or maleic anhydride modified polymers. Additionally or alternatively, the polymeric material further comprises one or more fillers, such as one or more organic fillers and/or one or more inorganic fillers (e.g., particulates of calcium carbonate, pigments, etc.). In accordance with certain embodiments of the invention, the polymeric material further comprises one or more slip agents, such as an amide. The one or more slip agents for example, may comprise a primary amide, a secondary amide, a tertiary amide, a bis-amide, or any combination thereof. In accordance with certain embodiments of the invention, the one or more slip agents may comprise one or more primary amides. By way of example, primary amides suitable as a slip agent in accordance with certain embodiments of the invention may comprise erucamide, oleamide, stearamide, behenamide, or any combination thereof. Alternatively or additionally, certain embodiments of the invention may comprise one or more slip agents comprising one or more secondary amides. By way of example, secondary amides suitable as slip agents in accordance with certain embodiments of the invention comprise oleyl palmitamide, stearyl erucamide, or any combination thereof. Alternatively or additionally, certain embodiments of the invention may comprise one or more slip agents comprising one or more bis-amides, such as ethylene bis-amides. By way of example, bis-amides suitable as a slip agents in accordance with certain embodiments of the invention comprise ethylene bis-stearamide, ethylene bis-oleamide, or any combination thereof. Slip agents, in accordance with certain embodiments of the invention, may comprise an amide (e.g., a primary amide, a secondary amide, a tertiary amide, bis-amide, etc.) including one or more saturated or unsaturated aliphatic chains. In accordance with certain embodiments of the invention, the one or more aliphatic chains may each independently comprise from about 1 to about 30 carbon atoms (e.g., about 5 to about 30 carbon atoms). For example, a secondary amides and bis-amides may comprise two saturated and/or unsaturated carbon chains the may each independently comprise from about 1 to about 30 carbon atoms (e.g., about 5 to about 30 carbon atoms). By way of example only, the one or more aliphatic chains may each independently comprise from at least about any of the following: 1, 5, 10, 15, 16, 17, 18, 19, 20, 21, 22, 23, 24, and 25 carbon atoms and/or at most about 30, 29, 28, 27, 26, 25, 20, and 15 carbon atoms (e.g., about 15 to about 25 carbon atoms, about 20 to 30 carbon atoms, etc.). In accordance with certain embodiments of the invention, the slip agent may comprise an amide including an unsaturated aliphatic chain having one or more elements or unsaturation. An element of unsaturation corresponds to two fewer hydrogen atoms than in the saturated formula. For example, a single double bound accounts for one element of unsaturation, while a triple bond would account for two elements of unsaturation. In accordance with certain embodiments of the invention, the slip agent includes an unsaturated aliphatic chain comprising from about 1 to about 10 elements of unsaturation (e.g., 1, 2, 3, 4, 5, 6, 7, 8, 9, or 10 elements of saturation).

In accordance with certain embodiments of the invention, the plurality of mono-component spunbond fibers comprise a round cross-section, non-round cross-section, or both. For example, non-round cross-section fibers may comprise a pie-shaped cross-section, a multilobal cross-section, or a ribbon-shaped cross-section. In accordance with certain embodiments of the invention, the plurality of mono-component spunbond fibers comprise a non-round cross-section having an aspect ratio of at least about 1.5:1, such as from about 1.5:1 to about 10:1.

In accordance with certain embodiments of the invention, the plurality of mono-component spunbond fibers define a first nonwoven layer, and the nonwoven fabric further comprises one or more additional nonwoven layers including, for example, at least a second nonwoven layer. In this regard, the nonwoven fabric may comprise a multilayer nonwoven fabric. The one or more additional layers, for example, may comprise a spunbond layer, a meltblown layer, a carded layer, a hydroentangled layer, a cellulosic layer, or any combination thereof. In accordance with certain embodiments of the invention, the nonwoven fabric includes one or more cellulosic layers located directly or indirectly between the first nonwoven layer and the second nonwoven layer, wherein the second nonwoven layer comprises a second spunbond layer or a spunbond-meltblown-spunbond layer.

For example, the nonwoven fabric may be provided as a component of a composite structure, such as a SMS-type nonwoven fabric. In this regard, the plurality of mono-component spunbond fibers may define a first spunbond nonwoven layer of a SMS structure, in which each 'S' may include from about 1 to about 5 spunbond layers and the 'M' may include from about 1 to about 5 meltblown layers. In accordance with certain embodiments of the invention, a second plurality of mono-component spunbond fibers may define a second spunbond nonwoven layer of a SMS structure. In this regard, each of the outermost spunbond layers maybe formed from mono-component spunbond fibers as described and disclosed herein. In accordance with certain embodiments of the invention, the onset of melting for the spunbond layer(s), such as those described and disclosed herein, is at least about 3° C. lower than a second onset of melting for the meltblown layer(s), such as at least about any 3, 5, 6, 8, and 10° C., and/or at most about any of the following: 40, 35, 30, 25, 20, 18, 15, 12, and 10° C. Stated somewhat differently, a difference between the onset of melting for the spunbond layer(s) and a second onset of melting for the meltblown layer(s) may be at least about 3° C., such as at least about any 3, 5, 6, 8, and 10° C., and/or at most about any of the following: 40, 35, 30, 25, 20, 18, 15, 12, and 10° C., in which the onset of melting for the spunbond layer(s) is lower than the second onset of melting for the meltblown layer(s).

In accordance with certain embodiments of the invention, the present invention provides an SMS construct, in which one or both of the outermost spunbond nonwoven layers are formed with a polymeric material and/or polymeric blend as described and disclosed herein. For example, the SMS construct may include a first spunbond layer, at least one meltblown layer, and at least a second spunbond layer, the at least one meltblown layer is located between the first spunbond layer and the second spunbond layer. The first spunbond layer includes the plurality of mono-component spunbond fibers and defines a first outermost spunbond nonwoven layer of the SMS construct. In accordance with certain embodiments of the invention, the second spunbond layer includes a second plurality of mono-component spunbond fibers and defines a second outermost spunbond nonwoven layer of the SMS construct, in which the second plurality of mono-component spunbond fibers are formed from an identical polymeric material or polymeric blend as the first spunbond layer. For example, each of the outermost spunbond nonwoven layers may be formed from a polymeric material and/or polymeric composition as described and disclosed herein.

In accordance with certain embodiments of the invention, the at least one meltblown layer may comprise a plurality of meltblown fibers comprising a meltblown polymeric composition including from 50% to 100% by weight of one or more polypropylenes and/or a polypropylene with a visbreaker, such as at least about any of the following: 50, 60, 70, 80, and 90% by weight, and/or at most about any of the following: 100, 99, 98, 96, 95, 94, 92, and 90% by weight. Additionally or alternatively, the meltblown polymeric composition may have a melt flow rate from about 500 to about 2000 g/10 min as determined by ASTM D1238 (230° C./2.16 kg), such as at least about any of the following: 500, 600, 700, 800, 900, 1000, 1100, and 1200 g/10 min as determined by ASTM D1238 (230° C./2.16 kg), and/or at most about any of the following: 2000, 1900, 1800, 1600, 1500, 1400, and 1200 g/10 min as determined by ASTM D1238 (230° C./2.16 kg).

In accordance with certain embodiments of the invention, the nonwoven fabric may have been thermally consolidated at a temperature below an onset of melting of the meltblown polymeric composition noted above with respect to the different in onset of melting points between the spunbond nonwoven layers and the at least one meltblown layer. For instance, the lower onset of melting for the spunbond nonwoven layers provides for the consolidation of the SMS construct at a temperature sufficient to bond the individual layers together to form the SMS construct, while not imparting holes (e.g., pinholes) in the meltblown layer. In accordance with certain embodiments of the invention, the plurality of meltblown fibers have not been softened or melted during the thermal bonding operation. In accordance with certain embodiments of the invention, the at least one meltblown layer is devoid of pinholes. In this regard, the present invention also provides a method of forming a SMS construct in which the SMS construct is consolidated at a temperature below that onset of softening and/or melting of the plurality of meltblown fibers. Such resulting SMS constructs may provide both high tensile strength and high hydrohead due to the lowered optimum bonding temperature of the spunbond nonwoven layer(s) preventing the formation of pinholes in the meltblown layer(s) (e.g., as compared to 100% PP spunbond nonwoven layers)

Moreover, the nonwoven fabric may be provided as a component of a composite structure, such as a nonwoven-film laminate. For example, the nonwoven fabric may be directly bonded to a polymeric film layer, such as a polyethylene film. The polymeric film layer may comprise a mono-layer film or a multi-layer film (e.g., core layer sandwiched between two skin layer). Additionally or alternatively, the polymeric film layer may comprises a microporous film and/or a monolithic film (e.g., devoid or substantially devoid of pores). In accordance with certain embodiments of the invention, the onset of melting for the spunbond layer(s), such as those described and disclosed herein, is at least about 3° C. lower than a third onset of melting for the polymeric film layer, such as at least about any 3, 5, 6, 8, and 10° C., and/or at most about any of the following: 40, 35, 30, 25, 20, 18, 15, 12, and 10° C. Stated somewhat differently, a difference between the onset of melting for the spunbond layer(s) and a third onset of melting for the polymeric film layer may be at least about 3° C., such as at least about any 3, 5, 6, 8, and 10° C., and/or at most about any of the following: 40, 35, 30, 25, 20, 18, 15, 12, and 10° C., in which the onset of melting for the spunbond layer(s) is lower than the third onset of melting for the polymeric film layer.

In accordance with certain embodiments of the invention, the nonwoven fabric has a basis weight of at least about 2 grams-per-square-meter (gsm), such as at least about any of the following: 2, 4, 5, 6, 8, 10, 12, 14, 15, 16, 18, 20, 22, 25, 28, 30, 32, 35, 38, 40, 42, 45, 48, 50, 52, 55, 58, and 60 gsm, and/or at most about any of the following: 100, 95, 90, 85, 80, 75, 70, 65, and 60 gsm.

In another aspect, the present invention provides a method of making a nonwoven fabric, such as those described and disclosed herein. The method may comprise the following: (a) forming a polymeric melt including a polymeric blend of (i) at least one polypropylene polymer, (ii) at least one polyethylene polymer, and (iii) at least one compatibilizer comprising or consisting of at least one polypropylene-polyethylene copolymer; (b) forming a plurality of mono-component spunbond fibers via melt-spinning the polymeric melt; and (c) consolidating the plurality of mono-component spunbond fibers to form a nonwoven fabric in accordance with nonwoven fabrics as described and disclosed herein.

In accordance with certain embodiments of the invention, the step of forming the polymeric melt comprises selecting and blending that at least one polypropylene polymer, the at least one polyethylene polymer, and the at least one compatibilizer at an elevated temperature, in which the MFR of the at least one polyethylene polymer is less than the MFR of the at least one polypropylene polymer at the elevated temperature (e.g., 230° C.) and a difference between the MFR of the at least one polypropylene polymer and the MFR of the at least one polyethylene polymer is less than about 35. For example, the difference between the MFR of the at least one polypropylene polymer and the MFR of the at least one polyethylene polymer may be from about 1 to about 35, such as at least about any of the following: 1, 3, 5, 8, 10, 12, 15, 18, and 20, and/or at most about any of the following: 35, 32, 20, 28, 26, 25, 24, 22, and 20. In accordance with certain embodiments of the invention, the elevated temperature comprises from about 190° C. to about 250° C., such as at least about any of the following: 190, 200, 210, and 215° C., and/or at most about any of the following: 250, 245, 240, 235, 230, 225, 220, and 215° C. In accordance with certain embodiments of the invention, the polymeric blend may be extruded and/or meltspun at one or more the above-referenced elevated temperatures. In accordance with certain embodiments of the invention, the polymeric blend may be extruded and meltspun at the same elevated temperature.

In accordance with certain embodiments of the invention, the step of consolidating the plurality of mono-component spunbond fibers may comprise a thermal bonding operation, an ultrasonic bonding operation, a mechanical bonding operation, an adhesive bonding operation, or any combination thereof. The consolidating step, for example, may comprise forming a plurality of individual bond sites by a thermal bonding operation or an ultrasonic operation. In this regard, the plurality of individual bond sites define a bonded area. The bonded area, for instance, may comprise from about 3% to about 30% of the nonwoven fabric, such as at least about any of the following: 3, 4, 5, 6, 8, 10, 12, 14, and 15%, and/or at most about any of the following: 30, 28, 26, 25, 24, 22, 20, 18, 16, and 15%. Additionally or alternatively, the step of forming the plurality of individual bond sites may be performed at temperature from about 120° C. to about 150° C., such as at least about any of the following: 120, 122, 124, 125, 126, 128, 130, 132, 134, and 135° C., and/or at most about any of the following: 150, 148, 146, 145, 144, 142, 140, 138, 136, and 135° C.

In yet another aspect, the present invention provides an article comprising one or more nonwoven fabrics as described and disclosed herein. The article may comprise an adult diaper, a baby diaper, a pull-up, of a feminine hygiene pad. In accordance with certain embodiments of the invention, the article may comprise a topsheet comprising a nonwoven fabric as described and disclosed herein.

EXAMPLES

The present disclosure is further illustrated by the following examples, which in no way should be construed as being limiting. That is, the specific features described in the following examples are merely illustrative and not limiting. For each of the tensile strength measurements and percent elongation measurements were performed according to WSP 110.4 (Newtons/5 cm) Edana type method (50 mm strip tensile).

(I)

Four separate samples were prepared, bonded at their optimum bonding temperature based, at least in part, on the polymeric composition from which the samples were formed. Each of the sample was subjected to the same bonding pattern. Each of the samples were subjected to a variety of tests to evaluate certain physical properties as well as softness properties.

Control:

A first nonwoven fabric (i.e., PP Control-140C in FIG. 1) of monocomponent fibers was formed from 100% by weight of a polypropylene homopolymer (i.e., PP3155E5 from Exxon) having a MFR of 36 g/10 min per ASTM D1238 (230° C./2.16 kg). This nonwoven fabric was thermally point bonded at a temperature of 140° C.

Example #1

A second nonwoven fabric (i.e., Example #1 in FIG. 1) of monocomponent fibers was formed from the following polymeric composition: (i) 80% by weight of a polypropylene homopolymer (i.e., PP3155E5 from Exxon) having a MFR of 36 g/10 min per ASTM D1238 (230° C./2.16 kg); (ii) 15% by weight of a linear low density polyethylene (i.e., PE-Dowlex 2036.01 G from Dow) having a MFR of 2.5 g/10 min per ASTM D1238 (190° C./2.16 kg); and (iii) 5% by weight of an EP-iPP diblock polymer (i.e., Intune™—Dow D5545) having a MFR of 9.5 g/10 min per ASTM D1238 (230° C./2.16 kg). This nonwoven fabric was thermally point bonded at a temperature of 135° C.

Comparative Example #1

A third nonwoven fabric (i.e., Comp. Ex. #1 in FIG. 1) of monocomponent fibers was formed from the following polymeric composition: (i) 93.5% by weight of a polypropylene homopolymer (i.e., PP3155E5 from Exxon) having a MFR of 36 g/10 min per ASTM D1238 (230° C./2.16 kg); (ii) 5% by weight of a Vistamaxx™ 6202FL, which has a MFR of 9.1 g/10 min per ASTM D1238 (230° C./2.16 kg). which is a polypropylene-based elastomer that comprises a random copolymer of propylene and ethylene; and (iii) 1.5% by weight of erucamide. This nonwoven fabric was thermally point bonded at a temperature of 140° C.

Comparative Example #2

A fourth nonwoven fabric (i.e., Comp. Ex. #2 in FIG. 1) of polypropylene-polyethylene bicomponent fibers having a sheath/core configuration with the sheath being formed from a polyethylene and the core being formed from a polypropylene homopolymer (i.e., PP3155E5 from Exxon) described above. The polyethylene was ASPUN™ 6850A from Dow. This nonwoven fabric was thermally point bonded at a temperature of 130° C.

Figure 1:
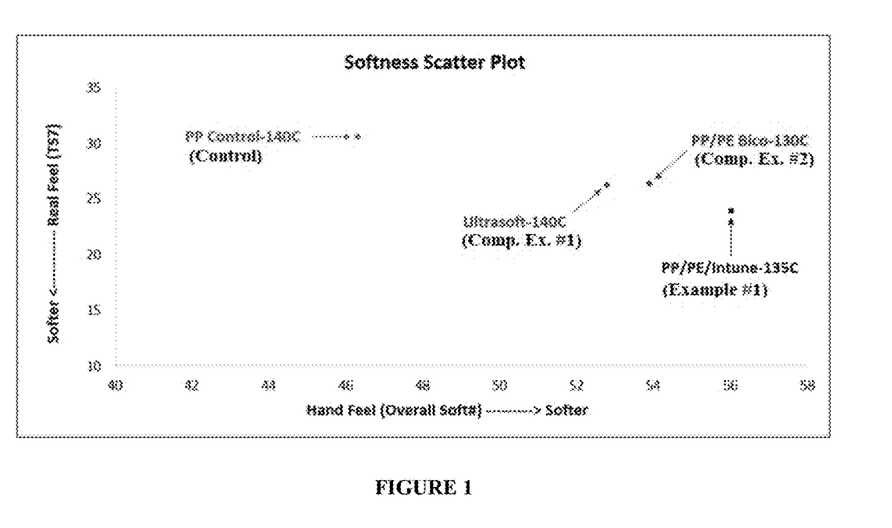
FIG. 1 shows a softness scatter plot for a variety of nonwoven fabrics.

FIG. 1 provides a summary of softness data as determined with a TSA—Tissue Softness Analyzer from Emtec Innovative Testing Solutions. In this regard, the "T57" data is a direct measurement of the softness of the sample (e.g., via measurement of blade vibration by the TSA device due to the stiffness of the fibers) and the "HF" values are composite values based on the "T57" data, a "TS750" data, and "D" data. The "HF" values provide an objective evaluation of the samples overall hand-feel. "TS750" data is a direct measurement of the samples roughness (e.g., via measurement of vertical vibrations from the sample by the TSA device due to horizontal blade movement across the surface of the sample. The "D" data is a direct measurement of the stiffness of the sample by the TSA device due to the sample deformation under a defined force.

As shown in FIG. 1, Example 1 had the lowest "T57" values, which as noted above is a direct measurement of the softness of a sample. Additionally, Example 1 had the largest HF value, which as noted above is an objective evaluation of a sample's overall hand-feel. In this regard, Example 1 outperformed the control sample as well as each of the comparative examples.

(II)

A variety of different nonwoven fabrics were formed from the polymeric compositions noted above. Physical properties and softness data was collected for each sample. The results are summarized in Table 1 below.

D1238 (230° C./2.16 kg). This nonwoven fabric was thermally point bonded at a temperature of 137° C.

Figure 3A:
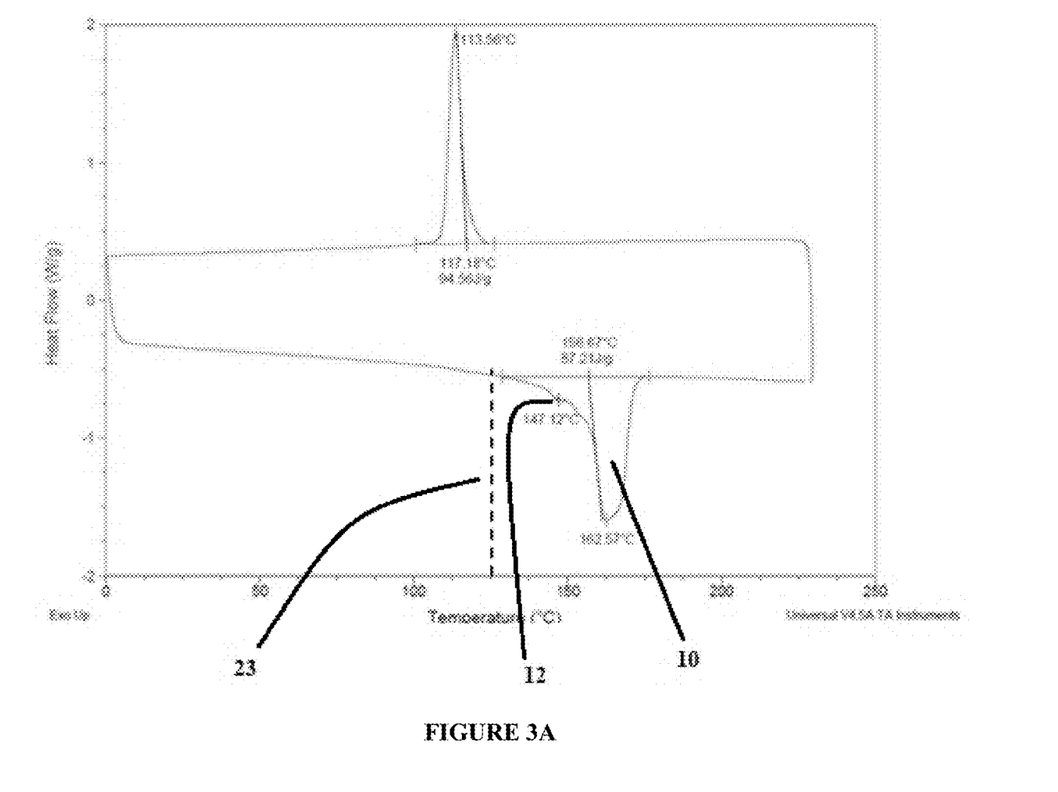
FIG. 3A shows a differential scanning calorimetry (DSC) curve for a control.

The polypropylene homopolymer used to form the monocomponent fibers of the control was subjected differential scanning calorimetry (DSC) as shown on FIG. 3A. As shown in FIG. 3A, the DSC curve includes a single peak 10 with an onset of melting 12 of approximately 147° C.

Example 1

A second nonwoven fabric (i.e., PP/PE/Intune in Tables 2 and 3) of monocomponent fibers was formed from the following polymeric composition: (i) 80% by weight of a polypropylene homopolymer (i.e., PP3155E5 from Exxon) having a MFR of 36 g/10 min per ASTM D1238 (230° C./2.16 kg); (ii) 15% by weight of a linear low density polyethylene (i.e., PE-Dowlex 2036.01G from Dow) having a MFR of 2.5 g/10 min per ASTM D1238 (190° C./2.16 kg); and (iii) 5% by weight of an EP-iPP diblock polymer (i.e., Intune™—Dow D5545) having a MFR of 9.5 g/10 min per ASTM D1238 (230° C./2.16 kg). This nonwoven fabric was thermally point bonded at a temperature of 130° C.

Figure 3B:
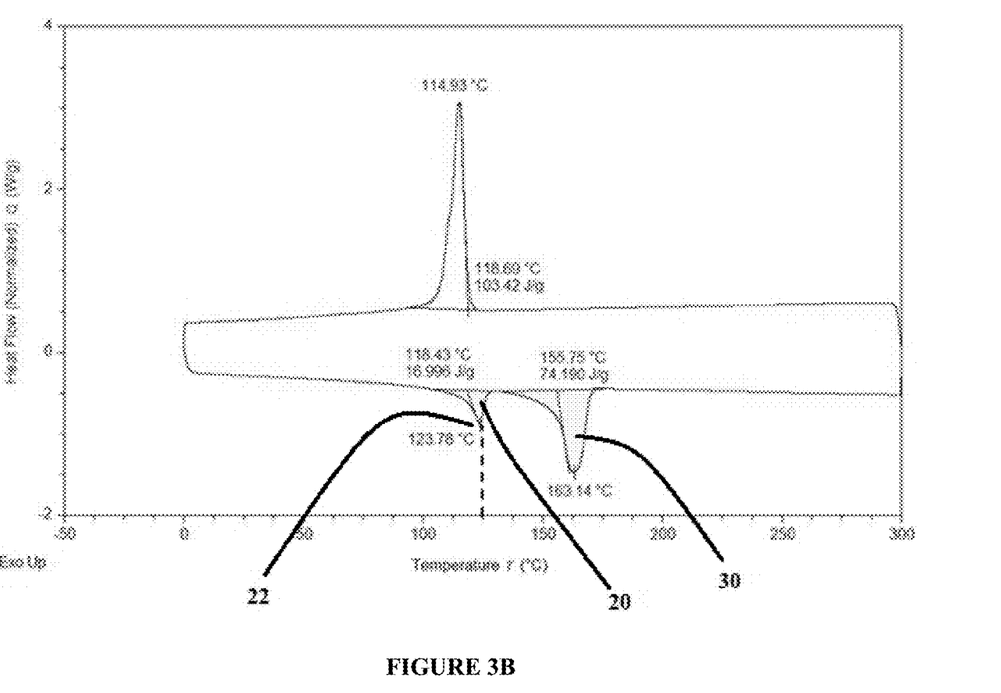
FIG. 3B shows a DSC curve for a polymeric composition in accordance with certain embodiments of the invention.

The polymeric composition used to form the monocomponent fibers of Example 1 was subjected differential scanning calorimetry (DSC) as shown on FIG. 3B. As shown in FIG. 3B, the DSC curve includes two prominent peaks. For instance, the DSC curve includes a first peak 20, which represents the melting of the polyethylene component, and a second peak 30, which is associated with the polypropylene component. The first peak 20 has an onset of melting of approximately 124° C. In this regard, the polymeric composition of Example 1 provides a significant reduction in an onset of melting, which enables the use of reduced calen-

TABLE 1

| Sample | Bond T (° C.) | BW (gsm) | MDT (N) | MDE (%) | CDT (N) | CDE (%) | (MDT + CDT)/BW ↑ | (MDE + CDE)/BW | MD/CD | HF ↑ | TS7 ↓ | D ↓ | CoF ↓ | FD(microns) |
|---|---|---|---|---|---|---|---|---|---|---|---|---|---|---|
| PP Control-140 C.[1] | 140 | 49.91 | 51.19 | 5.6 | 32.49 | 3.77 | 1.68 | 0.18 | 1.58 | 46.3 | 30.6 | 0.9 | 0.331 | 22.57 |
| PP/PE Bico-125 C.[2] | 125 | 48.59 | 55.18 | 36.32 | 32.54 | 40.18 | 1.81 | 1.39 | 1.7 | 74.7 | 15.2 | 1.7 | 0.206 | 22.8 |
| PP/PE Bico-130 C.[2] | 130 | 47.43 | 125.13 | 160.57 | 66.45 | 176.93 | 4.04 | 2.7 | 1.88 | 53.9 | 26.4 | 1.2 | 0.196 | 21.67 |
| PP/PE/Intune-125 C.[3] | 125 | 41.42 | 27.22 | 5.9 | 16.77 | 4.54 | 1.06 | 0.38 | 1.62 | 69.7 | 17.6 | 1.2 | 0.416 | 21.48 |
| PP/PE/Intune-130 C.[3] | 130 | 43.15 | 30.33 | 6.17 | 20.92 | 8.37 | 1.19 | 0.48 | 1.45 | 69.3 | 17.4 | 1.1 | 0.365 | 22.08 |
| PP/PE/Intune-135 C.[3] | 135 | 55.37 | 62.9 | 19.68 | 38.56 | 28.42 | 1.83 | 0.76 | 1.63 | 56 | 23.9 | 1.1 | 0.356 | 22.76 |
| Ultrasoft-125 C.[4] | 125 | 50.8 | 26.51 | 3.04 | 16.46 | 2.29 | 0.85 | 0.1 | 1.61 | 61.7 | 21.1 | 1.2 | 0.168 | 21.95 |
| Ultrasoft-130 C.[4] | 130 | 51.11 | 28.57 | 2.76 | 15.94 | 4.1 | 0.87 | 0.13 | 1.79 | 64.1 | 19.7 | 1.2 | 0.155 | 21.85 |
| Ultrasoft-135 C.[4] | 135 | 51.11 | 40.31 | 5.23 | 25.62 | 9.93 | 1.29 | 0.3 | 1.57 | 65.1 | 19.1 | 1.2 | 0.161 | 22.23 |
| Ultrasoft-140 C.[4] | 140 | 52.64 | 55.57 | 11.46 | 36.11 | 5.34 | 1.74 | 0.32 | 1.54 | 52.8 | 26.2 | 1 | 0.194 | 22.17 |

[1]indicates sample made according to 'control' from section (I) above;
[2]indicates sample made according to 'comparative example #2' from section (I) above with the proviso of bonding temperature shown in Table 1;
[3]indicates sample made according to 'example #1' from section (I) above with the proviso of bonding temperature shown in Table 1;
[4]indicates sample made according to 'comparative example #1' from section (I) above with the proviso of bonding temperature shown in Table 1;

(III)

Three separate samples were prepared and subjected to the same bonding pattern. Each of the samples were subjected to a variety of tests to evaluate softness properties, which are summarized in Table 2, as well as certain physical properties, which are summarized in Table 3 and illustrated in FIG. 2. The softness properties of "HF", "T57", and "D" values are determined as discussed above. The coefficient of friction CoF) was tested as per ASTM D1894 using the IMASS SP2000 equipment.

Control:

A first nonwoven fabric (i.e., Control PP Mono in Tables 2 and 3) of monocomponent fibers was formed from 100% by weight of a polypropylene homopolymer (i.e., PP3155E5 from Exxon) having a MFR of 36 g/10 min per ASTM dering temperatures (e.g., reduced bonding temperatures) while still providing good tensile properties as shown in Table 3. The approximate onset of melting for the polymeric composition of Example 1 has been superimposed by dashed line 23 on the DSC curve of FIG. 3A to help illustrate the reduction in onset of melting.

Example 2

A third nonwoven fabric (i.e., PP/PE/Intune/NHP01 in Tables 2 and 3) of monocomponent fibers was formed from the following polymeric composition: (A) a polymeric blend of (i) 80% by weight of a polypropylene homopolymer (i.e., PP3155E5 from Exxon) having a MFR of 36 g/10 min per ASTM D1238 (230° C./2.16 kg), (ii) 15% by weight of a linear low density polyethylene (i.e., PE-Dowlex 2036.01G from Dow) having a MFR of 2.5 g/10 min per ASTM D1238 (190° C./2.16 kg), and (iii) 5% by weight of an EP-iPP diblock polymer (i.e., Intune™—Dow D5545) having a MFR of 9.5 g/10 min per ASTM D1238 (230° C./2.16 kg); and (B) 1.5% of erucamide by weight of the polymeric composition. This nonwoven fabric was thermally point bonded at a temperature of 130° C.

TABLE 2

| Sample | Bond T (° C.) | BW (gsm) | HF (Higher = Softer) | TS7 (Lower = Softer) | D (Lower = Softer) | CoF (Lower = Softer) |
|---|---|---|---|---|---|---|
| Control PP Mono | 137 | 14.65 | 94.9 | 3.6 | 2.4 | 0.381 |
| PP/PE/Intune | 130 | 12.96 | 96.7 | 4 | 2.4 | 0.403 |
| PP/PE/Intune/NHP01 | 130 | 13.21 | 98.4 | 3.5 | 2.2 | 0.199 |

TABLE 3

| Sample | Bond T (° C.) | BW (gsm) | MDT (N) | MDE (%) | CDT (N) | CDE (%) | (MDT + CDT)/BW | (MDE + CDE)/BW |
|---|---|---|---|---|---|---|---|---|
| Control PP Mono | 137 | 14.65 | 20.84 | 51.21 | 11.33 | 51.68 | 2.2 | 7.02 |
| PP/PE/Intune | 130 | 12.96 | 24.11 | 66.51 | 19.17 | 66.87 | 3.34 | 10.29 |
| PP/PE/Intune/NHP01 | 130 | 13.21 | 11.52 | 81.22 | 10.89 | 70.65 | 1.7 | 11.5 |

Figure 2:
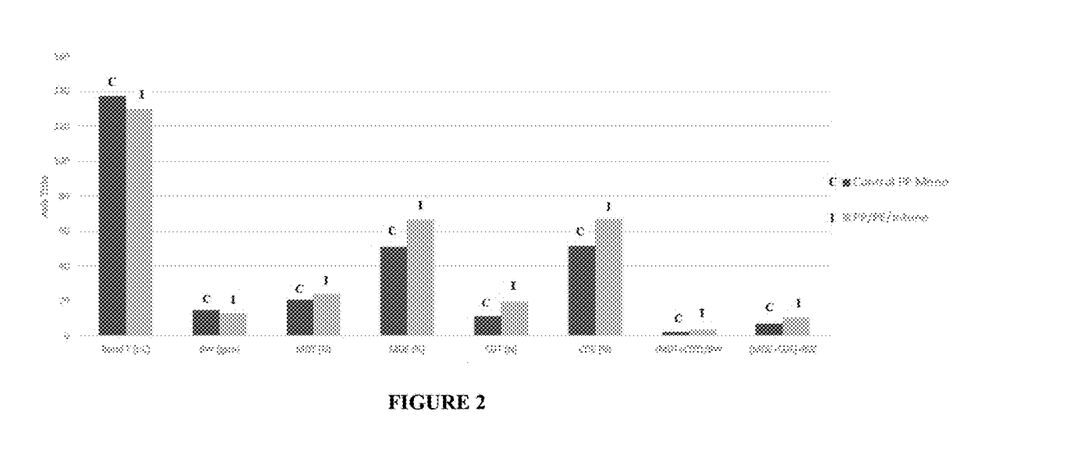
FIG. 2 shows physical property data for a control sample and a sample in accordance with certain embodiments of the invention.

As illustrated by Table 3 and FIG. 2, nonwoven fabrics formed from a polymeric blend in accordance with certain embodiments of the invention provide similar to improved tensile strengths while being bonded at a lower temperature.

These and other modifications and variations to the invention may be practiced by those of ordinary skill in the art without departing from the spirit and scope of the invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

That which is claimed:

1. A nonwoven fabric, comprising:
a plurality of mono-component spunbond fibers comprising a polymeric material including a polymeric blend of (i) at least one polypropylene polymer, (ii) at least one polyethylene polymer, and (iii) at least one compatibilizer comprising at least one polypropylene-polyethylene copolymer including a first polypropylene-polyethylene copolymer having an ethylene monomer content from about 5 to about 60% by weight and a melt flow rate (MFR) of from about 0.5 to about 20 g/10 min as determined by ASTM D1238 (230° C./2.16 kg);
wherein the nonwoven fabric has one or more of the following: (i) a TS7 value of at most about 30 as determined by a Tissue Softness Analyzer (TSA) from Emtec Innovative Testing Solutions; (ii) a HF value of at least about 40 as determined by a Tissue Softness Analyzer (TSA) from Emtec Innovative Testing Solutions; (iii) a delta value of at least 20, wherein the delta value is determined by subtracting the TS7 value from the HF value; (iv) a TS7 value that is from about 5% to about 35% lower than that of an identically constructed nonwoven fabric with the exception that the identically constructed nonwoven fabric is formed from 100% polypropylene; and (v) a HF value that is from about 5% to about 35% larger than that of an identically constructed nonwoven fabric with the exception that the identically constructed nonwoven fabric is formed from 100% polypropylene.

2. The nonwoven fabric of claim 1, wherein the nonwoven fabric has one or more of a TS7 value is from about 2 to about 30, a HF value from 40 to 120, a delta value from about 20 to about 75.

3. The nonwoven fabric of claim 1, wherein the polymeric blend comprises from about 60 to about 90 wt. % of the at least one polypropylene polymer, from about 5 to about 30 wt. % of the at least one polyethylene polymer, and from about 1 to about 10 wt. % of the at least one polypropylene-polyethylene copolymer.

4. The nonwoven fabric of claim 3, wherein the at least one polypropylene-polyethylene copolymer is a first polypropylene-polyethylene copolymer, the first polypropylene-polyethylene copolymer is a first block copolymer or a first EP-iPP diblock polymer.

5. The nonwoven fabric of claim 1, wherein a first MFR ratio between a first MFR of the at least one polypropylene polymer as determined by ASTM D1238 (230° C./2.16 kg) and a second MFR of the at least one polyethylene polymer as determined by ASTM D1238 (230° C./2.16 kg) is from about 5:1 to about 20:1.

6. The nonwoven fabric of claim 1, wherein the polymeric material further comprises a second compatibilizer comprising an anhydride functionality, one or more fillers, one or more slip agents, or any combination thereof.

7. The nonwoven fabric of claim 6, wherein the polymeric material includes one or more slip agents comprising a primary amide, a secondary amide, a tertiary amide, a bis-amide, or any combination thereof.

8. The nonwoven fabric of claim 1, wherein the plurality of mono-component spunbond fibers comprise a round cross-section, non-round cross-section, or both.

9. The nonwoven fabric of claim 1, wherein the plurality of mono-component spunbond fibers define a first nonwoven layer, and wherein the nonwoven fabric further comprises one or more additional nonwoven layers including at least a second nonwoven layer.

10. The nonwoven fabric of claim 9, wherein the one or more additional layers comprises a spunbond layer, a meltblown layer, a carded layer, a hydroentangled layer, a cellulosic layer, or any combination thereof.

11. The nonwoven fabric of claim 10, wherein the nonwoven fabric comprises a SMS construct including a first spunbond layer, at least one meltblown layer, and at least a second spunbond layer, the at least one meltblown layer is located between the first spunbond layer and the second spunbond layer; wherein the first spunbond layer includes the plurality of mono-component spunbond fibers and defines a first outermost spunbond nonwoven layer of the SMS construct.

12. The nonwoven fabric of claim 11, wherein the second spunbond layer includes a second plurality of mono-component spunbond fibers and defines a second outermost spunbond nonwoven layer of the SMS construct; wherein the second plurality of mono-component spunbond fibers are formed from an identical polymeric material or polymeric blend as the first spunbond layer.

13. The nonwoven fabric of claim 11, wherein the at least one meltblown layer comprises a plurality of meltblown fibers comprising a meltblown polymeric composition including from 50% to 100% by weight of one or more polypropylenes.

14. An article, comprising: a topsheet comprising a nonwoven fabric according to claim 1, wherein the article comprises an adult diaper, a baby diaper, a pull-up, of a feminine hygiene pad.

* * * * *